US00PP15164P2

(12) United States Plant Patent
Uchneat

(10) Patent No.: US PP15,164 P2
(45) Date of Patent: Sep. 21, 2004

(54) DOUBLE IMPATIENS PLANT NAMED 'BALOLEROSE'

(50) Latin Name: *Impatiens walleriana*
Varietal Denomination: Balolerose

(75) Inventor: Michael Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 14 days.

(21) Appl. No.: 10/736,725

(22) Filed: Dec. 16, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct Double Impatiens plant named 'Balolerose', characterized by its fully double pink-colored flowers, dark green-colored foliage, compact upright and mounded growth habit and excellent basal branching.

1 Drawing Sheet

Latin name of the genus and species of plant claimed: *Impatiens walleriana.*
Variety denomination: 'Balolerose'.

BACKGROUND OF THE INVENTION

The present invention relates to a new and distinct Double Impatiens plant botanically known as *Impatiens walleriana* and hereinafter referred to by the cultivar name 'Balolerose'.

The new cultivar was developed by the inventor in a controlled breeding program during November 2000 at Elburn, Ill. The objective of the breeding program was to develop new Impatiens cultivars with numerous fully double flowers, excellent basal branching, and upright, compact growth habit.

The female (seed) parent of 'Balolerose' was the proprietary *Impatiens walleriana* selection designated '3438-1' (not patented) characterized by its vigorous growth habit, purple-colored flowers, and dark green-colored foliage. The male (pollen) parent of 'Balolerose' was the proprietary *Impatiens walleriana* selection '3357-3' (not patented) characterized by its vigorous upright habit, fully double red-colored flowers, and dark green-colored foliage. 'Balolerose' was discovered and selected as one flowering plant within the progeny of the stated cross-pollination in September of 2001 and was initially designated '7544-4'.

Asexual reproduction of the new cultivar by terminal cuttings in West Chicago, Ill., has demonstrated that the characteristics of the new cultivar, as herein described, reproduce true to type and are firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any change in phenotype.

It was repeatedly found that the cultivar of the present invention:

1. Exhibits fully double dark pink-colored flowers,

2. Forms dark green-colored foliage,
3. Exhibits a good basal branching character, and
4. Exhibits a compact, upright and mounded growth habit.

Plants of the new cultivar differ from plants of the parents primarily in flower color.

Of the many commercially available Double Impatiens cultivars known to the inventor, 'Balolerose' is most similar to 'Sparkler Rose' (U.S. Plant Pat. No. 9,603). However, in side-by-side comparisons conducted in West Chicago, Ill., plants of the new cultivar differed from plants of 'Sparkler Rose' in the following characteristics:

1. Plants of 'Balolerose' are more floriferous than plants of 'Sparkler Rose'.
2. The flowers of the plants of 'Balolerose' have more petals than the flowers of the plants of 'Sparkler Rose', and
3. The flowers of the plants of 'Balolerose' are a uniform color while the flowers of the plants of 'Sparkler Rose' are bicolor.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Balolerose'. The plants were grown for 8 weeks in a greenhouse at West Chicago, Ill.

DETAILED DESCRIPTION

Figure 1:
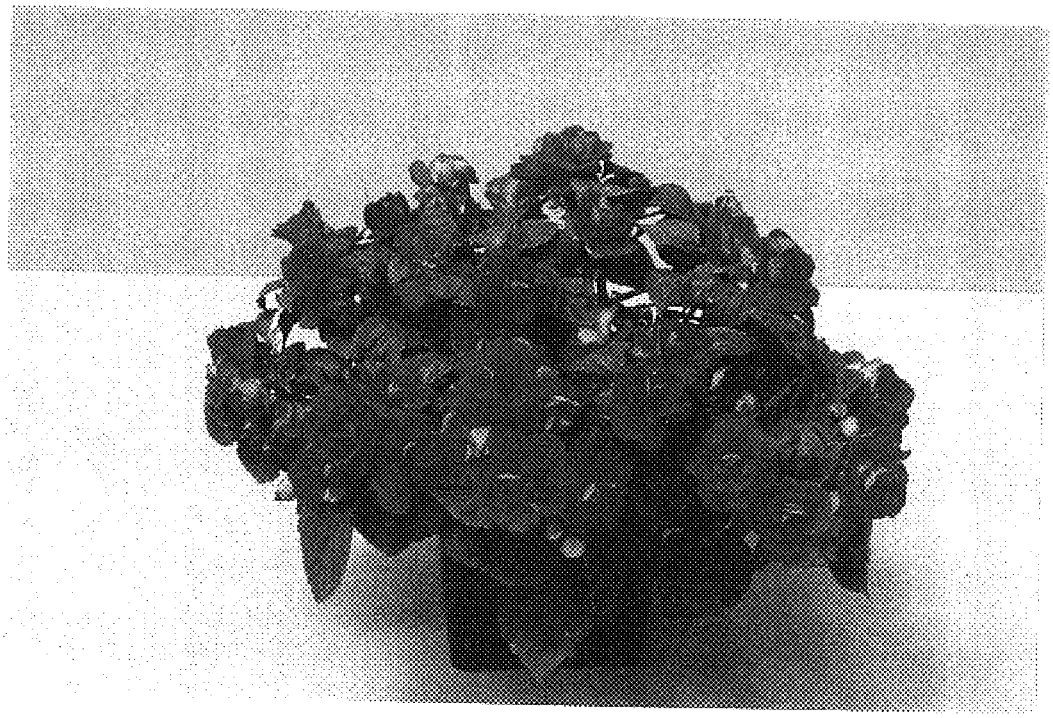
FIG. 1 illustrates a side view of the overall growth and flowering habit of 'Balolrose'.
Figure 2:
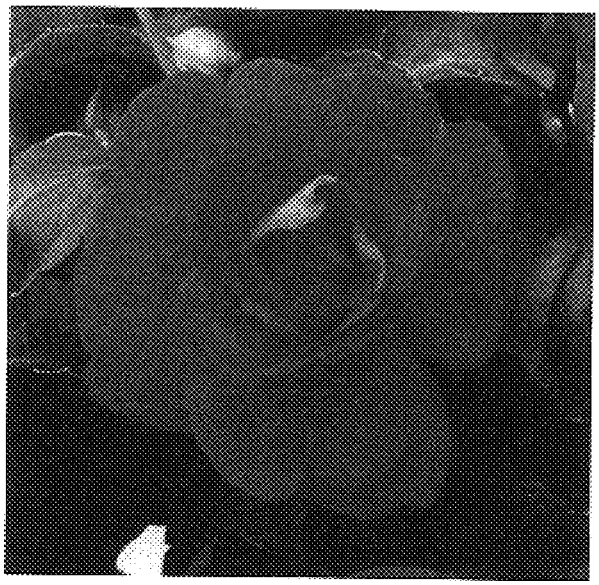
FIG. 2 illustrates a close up view of a single flower of 'Balolerose'.

The chart used in the identification of colors described herein is The R.H.S. Colour Chart of The Royal Horticultural Society, London, England, 1995 edition, except where general color terms of ordinary significance are used. The color values were determined on Jul. 16, 2003 between 10:00 and 11:45 a.m. under natural daylight conditions.

The following measurements and comparisons describe plants produced from cuttings taken from stock plants and grown under conditions comparable to those used in commercial practice. Plants were grown in 10 cm pots for 8 weeks while utilizing a soilless growth medium. Greenhouse temperatures were maintained at approximately 65°–75° F. during the day and approximately 55°–62° F. during the night. Greenhouse light levels were maintained at approximately 4,000–6,000 footcandles.

Botanical classification: *Impatiens walleriana* cultivar 'Balolerose'.

Parentage:

*Female (seed) parent*.—Proprietary *Impatiens walleriana* selection designated '3438-1'.

*Male (pollen) parent*.—Proprietary *Impatiens walleriana* selection designated '3357-3'.

Propagation:

*Type cutting*.—Terminal tip.

*Time to initiate roots*.—Approximately 7–14 days with the shorter times generally being experienced in the summer and the longer times in the winter.

*Time to develop roots*.—Approximately 21 days.

*Root description*.—Fine, fibrous.

*Rooting habit*.—Freely branching.

Plant description:

*Habit of growth*.—Compact with good basal branching. A mature plant, 8 weeks after the planting of a rooted cutting, commonly measures approximately 21.8 cm in height and approximately 33.6 cm in width (plant spread).

*Plant form*.—Upright and mounded.

*Lateral branches*.—Quantity: Approximately 3 per plant. Length: Approximately 15.7 cm. Diameter: Approximately 9 mm. Texture: Glabrous. Color: 148B with stripes and spots of 183A, especially around nodes. Internode length: Approximately 2.3 cm.

*Foliage*.—Type: Simple. Arrangement: Alternate. Shape: Ovate. Apex: Acuminate. Base: Attenuate. Margin: Crenate/cilate. Texture: Glabrous. Venation pattern: Pinnate, arcuate. Size of mature foliage: Length: Approximately 4.5 cm. Width: Approximately 2.9 cm. Color of mature foliage: Upper surface: 147A with veins and mid-vein of 146C. Lower surface: 146B with blotches of 176B and veins of 146C. Petiole: Length: Approximately 1.5 cm. Petiole diameter: 2 mm. Petiole texture: Both surfaces are glabrous. Petiole color: Both surfaces are 147C.

Flowering description:

*Flowering habit*.—Freely flowering.

*Natural flowering season*.—Year round in greenhouse environment. Flowering is continuous from spring until fall in the garden.

*Lastingness of individual bloom*.—Approximately 5–7 days.

*Quantity of flowers*.—Approximately 7 flowers and 7 buds per stem.

*Flower bud rate of opening*.—Generally it takes 7–10 days for buds to progress from first color to fully open flowers.

*Mature flower buds (just before opening)*.—Shape: Ovoid. Length: Approximately 1.3 cm. Diameter: Approximately 9 mm. Color of petals: 52C.

*Flower description*.—Type — Fully double. Shape: Round. Diameter: Approximately 4.1 cm. Depth: Approximately 2.3 cm. Aspect: Slightly cupped. Borne: Above foliage arising from leaf axils and facing upward or outward. Flowers are not persistent or fragrant.

*Petals*.—Arrangement: Imbricate. Number per flower: Approximately 33. Margin: Entire. Apex: Obtuse. Base: Attenuate. Texture: Smooth. Appearance: Iridescent. Size of outermost petals: Length: 2.2 cm. Width: 1.9 cm. Size of innermost petals: Length: 1.5 cm. Width: 1.3 cm.

*Flower color*.—Upper surface of petals when first opening: N57C. Lower surface of petals when first opening: 52C. Upper surface of petals when fully opened: N57A with base of 59B. Lower surface of petals when fully opened: 52C. Petal color fading to: 72C.

*Calyx*.—Quantity of sepals: Three with lower sepal modified into a spur. Apex: Acuminate. Texture of both surfaces: Glabrous. Lateral sepal shape: Lanceolate. Lateral sepal length: Approximately 3 mm. Lateral sepal width: Approximately 1 mm. Later sepal color: Both surfaces are 144C. Lower sepal shape: Ovate. Lower sepal length: Approximately 1 cm. Lower sepal width: Approximately 9 mm. Lower sepal color: 150D with tip of 150C.

*Spur*.—Quantity: One per flower. Length: Approximately 3.3 cm. Diameter at base: Approximately 2 mm. Diameter at tip: Approximately 0.4 mm. Color: 182C.

*Peduncles*.—Length: Approximately 1.6 cm. Diameter: Approximately 1 mm. Texture: Glabrous. Strength: Strong. Angle to stem: Acute. Color: 152D.

*Reproductive organs*.—None observed.

Seed and fruit development: Neither seed nor fruit production has been observed.

Disease and pest resistance: Resistance to pathogens and pests common to impatiens has not been observed.

What is claimed is:

1. A new and distinct cultivar of Double Impatiens plant named 'Balolerose' substantially, as herein shown and described, which:

1. Exhibits fully double pink-colored flowers,
2. Forms dark green-colored foliage,
3. Exhibits a good basal branching character, and
4. Exhibits a compact upright mounded growth habit.

* * * * *